United States Patent [19]

Coffen

[11] Patent Number: 4,483,990
[45] Date of Patent: Nov. 20, 1984

[54] PREPARATION OF DIKETONES

[75] Inventor: David L. Coffen, Glen Ridge, N.J.

[73] Assignee: Hoffman-La Roche Inc., Nutley, N.J.

[21] Appl. No.: 363,333

[22] Filed: Mar. 29, 1982

[51] Int. Cl.³ .......................................... C07D 217/04
[52] U.S. Cl. .................................... 546/149; 546/85
[58] Field of Search ................................ 546/149, 150

[56] References Cited
PUBLICATIONS

Grethe, *Isoquinolines*, Part One, 1981, John Wiley & Sons, N.Y., pp. 252–253.

*Primary Examiner*—Glennon H. Hollrah
*Assistant Examiner*—James H. Turnipseed
*Attorney, Agent, or Firm*—Jon S. Saxe; Bernard S. Leon; Matthew Boxer

[57] ABSTRACT

The preparation of bicyclic diketones of the formula

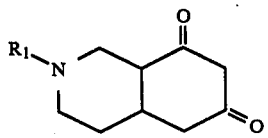

wherein $R_1$ is lower alkyl or ar-lower alkyl, from compounds of the formula

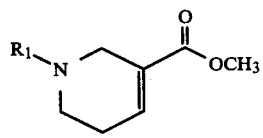

wherein $R_1$ is as set forth above, is described.

3 Claims, No Drawings 4,483,990

1

PREPARATION OF DIKETONES

BRIEF SUMMARY OF THE INVENTION

The invention relates to a process for the preparation of bicyclic diketones of the formula

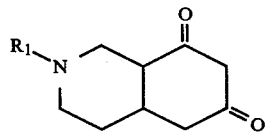

wherein $R_1$ is lower alkyl or ar-lower alkyl which comprises combining a compound of the formula

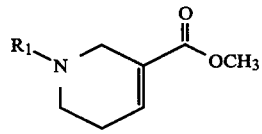

wherein $R_1$ is as previously described, with a compound of the formula

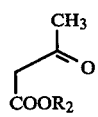

wherein $R_2$ is lower alkyl in a reaction sequence that consists of Michael addition, cyclization, hydrolysis, and decarboxylation.

DETAILED DESCRIPTION OF THE INVENTION

The invention relates to a facile process for the preparation of bicyclic diketones. More specifically, the process comprises the reaction of a compound of the formula

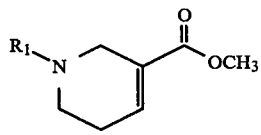

wherein $R_1$ is lower alkyl or ar-lower alkyl, with an acetoacetic acid ester of the formula

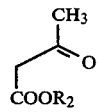

wherein $R_2$ is lower alkyl, under the reaction conditions hereinafter described, to yield a compound of the formula

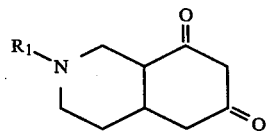

2 wherein $R_1$ is as previously described.

As used herein, the term lower alkyl denotes an alkyl group of 1 to 7 carbon atoms, for example, methyl, ethyl, propyl, isopropyl, butyl, pentyl, heptyl and the like. The term "ar-lower alkyl" denotes an aromatic hydrocarbon such as an aryl-lower alkyl, wherein aryl is phenyl or substituted phenyl and lower alkyl is as described herein. The substituents on the phenyl moiety may comprise one or more halogen, lower alkyl and the like. Exemplary of ar-lower alkyl are benzyl, methylbenzyl and the like.

In accordance with the invention, the process for the preparation of the compounds of formula I is carried out as set forth in Reaction Scheme I which follows:

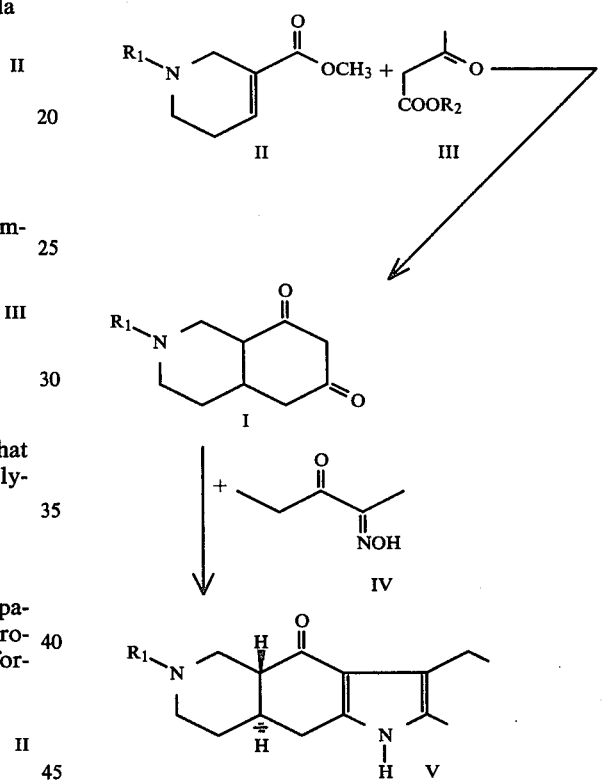

wherein $R_1$ and $R_2$ are as previously described.

In Reaction Scheme I, a compound of formula II is reacted with an acetoacetic acid ester of formula III in a solvent, for example, an alkanol, such as, methanol, ethanol, propanol, t-butyl alcohol and the like, and in the presence of an alkali metal alkoxide, such as, sodium ethoxide, potassium methoxide, potassium t-butoxide and the like. The compounds of formulas II and III are known compounds or can be prepared in accordance with known procedures. Exemplary of the compounds of formula II are methyl 1,2,5,6-tetrahydro-1-methylnicotinate (arecoline) and the like. At this stage of the process, a carbanion derived from the acetoacetic acid ester undergoes Michael addition to the $\alpha,\beta$-unsaturated ester function of compound II. The adduct thus formed undergoes cyclization under the reaction conditions employed.

Thereafter, the reaction mixture is treated sequentially with a base, for example, an alkali metal hydroxide, such as, sodium hydroxide, potassium hydroxide and the like, and an acid, for example, an inorganic acid, such as, hydrochloric acid, hydrobromic acid and the like. This treatment effects hydrolysis and decarboxylation, respectively, of the ester function introduced with the acetoacetic acid ester to yield a hexahydro-6,8(1H,7H)-isoquinolinedione of formula I.

The process of Reaction Scheme I is carried out at a temperature in the range of from about room temperature to about the reflux temperature of the reaction mixture. The desired hexahydro-6,8(1H,7H)-isoquinolinedione of formula I can be used in the subsequent reaction without separation. Alternatively, the desired hexahydro-6,8(1H,7H)-isoquinolinedione can be recovered and purified utilizing conventional methods, for example, ion exchange chromatography and the like. The compounds of formula I are known compounds. Exemplary of the compounds of formula I are hexahydro-2-methyl-6,8(1H,7H)-isoquinolinedione, hexahydro-2-benzyl-6,8(1H,7H)-isoquinolinedione, hexahydro-2-ethyl-6,8(1H,7H)-isoquinolinedione and the like.

The compounds of formula I are useful as intermediates to prepare, for example, 4,4a,5,6,7,8,8a,9-octahydro-4a,8a-trans-1H-pyrrolo[2,3-g]isoquinolin-4-ones of the formula V, as also illustrated in Reaction Scheme I. More specifically, a hexahydro-6,8(1H,7H)-isoquinolinedione of formula I is reacted with the 2-oximino-3-pentanone of formula IV, utilizing the conditions of a Knorr pyrrole synthesis, to yield the correspondingly substituted 4,4a,5,6,7,8,8a,9-octahydro-4a,8a-trans-1H-pyrrolo[2,3-g]isoquinolin-4-one.

The reaction is carried out, for instance, in the presence of zinc dust and an acid, for example, acetic acid, at a temperature in the range of from about room temperature to about the reflux temperature of the reaction mixture. The desired 4,4a,5,6,7,8,8a,9-octahydro-4a,8a-trans-1H-pyrrolo[2,3-g]isoquinolin-4-one of formula V is recovered utilizing conventional methods, for example, by crystallization and the like. The conversion of a compound of formula I to a 4,4a,5,6,7,8,8a,9-octahydro-4a,8a-trans-1H-pyrrolo[2,3-g]isoquinolin-4-one is further described in U.S. Pat. No. 4,260,762, issued Apr. 7, 1981. The 4,4a,5,6,7,8,8a,9-octahydro-4a,8a-trans-1H-pyrrolo[2,3-g]isoquinolin-4-ones are useful as antipsychotic agents, for instance, in the treatment of schizophrenia.

The examples which follow further illustrate the invention. All temperatures are in degrees centigrade unless otherwise stated.

EXAMPLE 1

Preparation of methyl 1,2,5,6-tetrahydro-1-methylnicotinate (Arecoline)

Methyl 1,2,5,6-tetrahydro-1-methylnicotinate hydrobromide (Arecoline HBr) weighing 350 g, was dissolved in 600 ml of water. To this solution 50 g of sodium chloride was added and allowed to dissolve. To this solution approximately 400 ml of saturated sodium carbonate solution was added and the mixture extracted four times with (4×) 500 ml of ether. The combined ether extracts were dried over sodium sulfate and the ether evaporated under reduced pressure using a 40° water bath. The methyl 1,2,5,6-tetrahydro-1-methylnicotinate was distilled under aspirator vacuum to give 188 g (82%) of a pale yellow liquid with b.p. 85°/20 mm (pressure approximate). The free base was stored in a freezer.

EXAMPLE 2

Preparation of hexahydro-2-methyl-6,8(1H,7H)-isoquinolinedione

Potassium metal weighing 83 g was washed free of oil with petroleum ether, weighed out in petroleum ether, and added to a 3 l-one neck flask containing 1800 ml of t-butyl alcohol. The potassium dissolved during several hours (approximately 8) of heating at reflux with magnetic stirring under argon. Thereafter, 140 g of distilled methyl acetoacetate was added to the cooled potassium t-butoxide solution followed by 160 g of methyl 1,2,5,6-tetrahydro-1-methylnicotinate. The resulting red solution was stirred under argon at room temperature for 24 hours and then at reflux for 48 hours. A solution of 300 g of potassium hydroxide in 700 ml of water was added carefully in portions with the condenser set down for distillation. Heating and stirring were continued for approximately 2 hours during which 1750 ml of distillate, wet t-butyl alcohol, was collected between 80°-94°.

With continued refluxing in a vertical condenser, 800 ml of concentrated hydrochloric acid was added in very small portions. Vigorous spattering and degassing accompanied the initial additions. The condenser was again set down and boiling continued for 1 hour during which an additional 100 ml of distillate was collected. The solution was cooled and concentrated as much as possible on the rotary evaporator using aspirator vacuum. Optional extraction, after cooling, with ether will remove most of the 1,3-dimethyl-2-pyridone by-product at this point.

EXAMPLE 3

Preparation of 3-ethyl-2,6-dimethyl 4,4a,5,6,7,8,8a,9-octahydro-1H-pyrrolo[2,3-g]isoquinolin-4-one hydrochloride The salt mixture from Example 2, in the same flask was taken up into 1800 ml of glacial acetic acid and cooled in an ice bath. Then, 40 g of 2-oximino-3-pentanone and 45 g of zinc dust were added and the cold mixture was stirred for 15 minutes. A mechanical stirrer was used for this step. The mixture was then stirred at reflux for 15 minutes then cooled again in an ice bath. Forty g (40 g) of 2-oximino-3-pentanone and 45 g of zinc dust were added and the mixture stirred 15 minutes while kept cold. It was heated to reflux for 15 minutes, again cooled in ice and a third portion of 40 g of 2-oximino-3-pentanone and 45 g of zinc dust added. After another 15 minutes of stirring while cold, the mixture was heated to reflux again and kept at reflux for 75 minutes. The batch was left at room temperature overnight at this point. Most of the acetic acid was removed using a rotary evaporator and aspirator vacuum. To the residue, there was added 1250 ml of 3N hydrochloric acid and 1050 ml of water to dissolve the residue.

The solution was transferred to a 4 l separatory funnel and washed three times with (3×) 1000 ml of ether. The ether layer from each wash was discarded, and 1500 ml of concentrated aqueous ammonia was added to the aqueous layer to make it strongly basic while keeping the zinc salts in solution. The crude product separated as a solid precipitate. It was collected, washed with water, and air-dried overnight to give 38.3 g of light yellow powder. An additional 1.6 g of crude product was extracted from the filtrate and washings as described below to give a overall crude yield of 39.9 g=15.7%. The aqueous filtrate and washings were extracted three times with (3×) 1000 ml of methylene chloride. The residue from the extract after drying with sodium sulfate and evaporation was about 100 ml of brown oil. Volatile by-products in this fraction were vacuum distilled off at 45°–75°/0.05 mm. The distillation residue was taken up in 100 ml of ether and chilled overnight to give, after filtering, washing with ether and air-drying, 1.6 g of additional crude product.

The 38.3 g of dried precipitate was taken up in 500 ml of hot ethanol and filtered through Celite to remove some insoluble material. The Celite cake was washed twice with (2×) 100 ml of hot ethanol. The filtered solution was concentrated to about 250 ml by boiling. After chilling overnight in a −40° freezer, the solid was collected, washed with ether and air-dried to give 20.0 g of reddish, crystalline product which is pure by thin layer chromatography. Evaporation of solvent from the filtrate and washings left a dark, semi-solid mush. This was triturated with ether, filtered and the solid washed with ether to give 4.7 g of "second crop" material. By combining this material and the 1.6 g fraction with the 20 g of once recrystallized product, 26.2 g of product was recrystallized by dissolving in a boiling solvent mixture of 300 ml of methylene chloride and 200 ml of ethanol. 2 g of charcoal was added and the solution was left for 20 minutes. After filtration through Celite and washing the cake twice with (2×) 50 ml of 1:1 methylene chloride-ethanol, the solution was boiled down to about 250 ml during which much of the product crystallized. After chilling in a −40° freezer for 4 hours, the product was collected, washed with ether, and air-dried to give 20.0 g of pink crystals with m.p. 260°–5° (some decomp.). Thereafter, 20.0 g of twice recrystallized 3-ethyl-2,6-dimethyl-4,4a,5,6,7,8,8a,9-octahydro-1H-pyrrolo[2,3-g]isoquinolin-4-one was treated with a solution of 10 ml of concentrated hydrochloric acid diluted to 100 ml with ethanol. The resulting mixture was heated on the steam bath giving a clear red solution. This was gradually diluted to 1000 ml with ether, adding small portions until precipitation commenced. The mixture was kept in the −40° freezer for 1 hour and then filtered. The solid was washed twice with ether and air-dried to give 23.04 g of very pale pink powder with m.p. 185°–8°. After vacuum drying overnight at 85°, the 3-ethyl-2,6-dimethyl-4,4a,5,6,7,8,8a,9-octahydro-1H-pyrrolo[2,3-g]isoquinolin-4-one hydrochloride weighed 22.3 g (6% based arecoline HBr).

I claim:

1. Process for the preparation of a bicyclic diketone of the formula

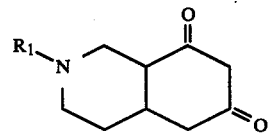

wherein $R_1$ is lower alkyl or ar-lower alkyl, which comprises the steps of
   (a) reacting a compound of the formula

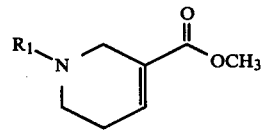

wherein $R_1$ is as previously described, with a compound of the formula

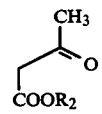

wherein $R_2$ is lower alkyl, in the presence of an alkali metal alkoxide; and
   (b) treating sequentially the reaction mixture of step (a) with a base and then with an acid to yield a compound of formula I.

2. A process in accordance with claim 1, wherein the compound of formula II is methyl 1,2,5,6-tetrahydro-1-methylnicotinate.

3. A process in accordance with claim 2, wherein the compound of formula III is methyl acetoacetate.

* * * * *